United States Patent [19]

Blaney

[11] 4,352,802
[45] Oct. 5, 1982

[54] BICYCLO[3.3.1]NONYL-BENZAMIDE

[75] Inventor: Frank E. Blaney, London, England

[73] Assignee: Beecham Group Limited, England

[21] Appl. No.: 268,741

[22] Filed: Jun. 1, 1981

[30] Foreign Application Priority Data

Jun. 10, 1980 [GB] United Kingdom ............... 8019017

[51] Int. Cl.³ .................. A61K 31/54; A61K 31/535; C07D 279/16; C07D 265/36
[52] U.S. Cl. ................................ 424/246; 424/248.5; 424/248.54; 544/47; 544/105
[58] Field of Search ............... 544/47, 105; 424/246, 424/248.54, 248.5

[56] References Cited

U.S. PATENT DOCUMENTS 2,970,144 1/1961 Zirkle ................................ 544/47
3,075,977 1/1963 Zirkle ................................ 544/47
3,856,783 12/1974 Miller ................................ 544/105

Primary Examiner—John M. Ford
Attorney, Agent, or Firm—Jacobs & Jacobs

[57] ABSTRACT

Compounds of the formula (I) and pharmaceutically acceptable salts thereof:

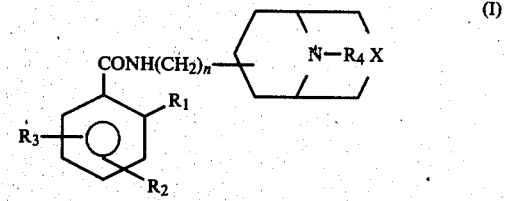

wherein:
X is oxygen or sulphur;
$R_1$ is a $C_{1-6}$ alkoxy or $C_{1-6}$ alkylthio group;
$R_2$ and $R_3$ are the same or different and are hydrogen, halogen, $CF_3$, $C_{1-7}$ acyl, $C_{1-7}$ acylamino or amino, aminocarbonyl or aminosulphonyl optionally substituted by one or two $C_{1-6}$ alkyl groups, $C_{1-6}$ alkylsulphonyl, $C_{1-6}$ alkylsulphinyl, $C_{1-6}$ alkoxy, $C_{1-6}$ alkylthio, hydroxy or nitro or $R_1$ and $R_2$ taken together are methylenedioxy or ethylenedioxy in which case $R_3$ is any one of the groups given for $R_2$ and $R_3$ above;
$R_4$ is $C_{1-7}$ alkyl or a group $-(CH_2)_sR_5$ where s is 0 to 2 and $R_5$ is a $C_{3-8}$ cycloalkyl group, or a group $-(CH_2)_tR_6$ where t is 1 or 2 and $R_6$ is a phenyl group optionally substituted by one or two substituents selected from $C_{1-6}$ alkyl, $C_{1-4}$ alkoxy, trifluoromethyl and halogen, or a thienyl group; and
n is 0 to 2; and there are at least two carbon atoms between the benzamide and heterogranatane ring nitrogen atoms, having useful pharmacological activity, pharmaceutical compositions contain them and process for their preparation.

13 Claims, No Drawings

BICYCLO[3.3.1]NONYL-BENZAMIDE

This invention relates to novel substituted benzamides having useful pharmacological properties, to pharmaceutical compositions containing them, and to a process for their preparation.

N-(2-Diethylaminoethyl)-2-methoxy-4-amino-5-chlorobenzamide, 1-ethyl-2(2-methoxy-5-sulphamoyl-benzamidomethyl)pyrrolidine and N-[4'-(1''-benzyl)-piperidyl]-2-methoxy-4-amino-5-chlorobenzamide are well known compounds having useful pharmacological activity such as the ability to regulate the gastro-intestinal function, anti-emetic activity and CNS activity.

It has now been found that a certain structurally distinct class of substituted benzamides also has useful pharmacological activity, in particular dopamine antagonist activity.

Accordingly the present invention provides compounds of the formula (I) and pharmaceutically acceptable salts thereof:

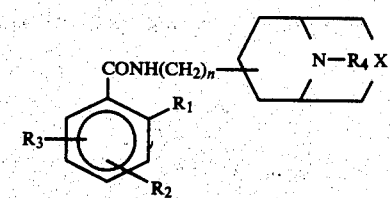

wherein:

X is oxygen or sulphur;

$R_1$ is a $C_{1-6}$ alkoxy or $C_{1-6}$ alkylthio group;

$R_2$ and $R_3$ are the same or different and are hydrogen, halogen, $CF_3$, $C_{1-7}$acyl, $C_{1-7}$ acylamino or amino, aminocarbonyl or aminosulphonyl optionally substituted by one or two $C_{1-6}$ alkyl groups, $C_{1-6}$ alkylsulphonyl, $C_{1-6}$ alkylsulphinyl, $C_{1-6}$alkoxy, $C_{1-6}$ alkylthio, hydroxy or nitro or $R_1$ and $R_2$ taken together are methylenedioxy or ethylenedioxy in which case $R_3$ is any one of the groups given for $R_2$ and $R_3$ above;

$R_4$ is $C_{1-7}$ alkyl or a group —$(CH_2)_sR_5$ where s is 0 to 2 and $R_5$ is a $C_{3-8}$ cycloalkyl group, or a group —$(CH_2)_tR_6$ where t is 1 or 2 and $R_6$ is a phenyl group optionally substituted by one or two substituents selected from $C_{1-6}$ alkyl, $C_{1-4}$alkoxy, trifluoromethyl and halogen, or a thienyl group; and n is 0 to 2; and there are at least two carbon atoms between the benzamide and heterogranatane ring nitrogen atoms.

Suitable examples of the group $R_1$ include methoxy, ethoxy and n- and iso-propoxy, methylthio, ethylthio, and n- and iso-propylthio. Preferably $R_1$ is a methoxy group.

Suitable examples of the groups $R_2$ and $R_3$ include the following groups: hydrogen, chlorine, bromine, amino, $C_{1-4}$ alkanoylamino such as formylamino, acetylamino, propionylamino, n- and iso-butyrylamino, aminosulphonyl, and amino and aminosulphonyl substituted by one or two methyl, ethyl, n- or iso-propyl, n-, sec- or tert-butyl groups, nitro, methoxy, ethoxy, n- and isopropoxy, methylthio, ethylthio, n and iso-propylthio, and hydroxy.

When $R_2$ and $R_3$ are other than hydroxy, $C_{1-6}$ alkoxy or $C_{1-6}$ alkylthio, it is generally preferred than $R_2$ is in the 4-position relative to the heterogranatyl (alkyl) aminocarbonyl side chain for greater activity in the resultant compound of the formula (I). For the same reason it is generally preferred that $R_3$ is in the 5-position relative to the same acylamino side chain. When one of $R_2$ and $R_3$ is $C_{1-6}$ alkoxy, it is preferably methoxy and the other is hydrogen.

Particularly preferred $R_2$ groups include 4-amino and 4-(acylated amino), especially 4-acetylamino as defined. Preferably $R_2$ is 4-amino or 4-acetylamino. Particularly preferred $R_3$ groups include 5-halo, such as 5-chloro.

Alternatively very suitably $R_2$ is hydrogen, amino or acylated amino, and $R_3$ is $C_{1-6}$ alkylsulphonyl, $C_{1-6}$ alkylsulphinyl, or aminosulphonyl optionally substituted by one or two $C_{1-6}$ alkyl groups. In such cases, as above preferably $R_2$ is in the 4-position and $R_3$ is in the 5-position; and preferred examples of $R_2$ include hydrogen and of $R_3$ include methylsulphonyl, methylsulphinyl and aminosulphonyl.

When $R_1$ and $R_2$ taken together are methylenedioxy or ethylenedioxy $R_1$ and $R_2$ are preferably ethylenedioxy.

Suitable examples of $R_4$ when $C_{1-7}$ alkyl include methyl, ethyl, n- and iso- and n, sec- and tert-butyl. Within $C_{1-7}$ alkyl, $C_{5-7}$ alkyl are of interest and suitable examples thereof include n-pentyl, n-hexyl and n-heptyl and 3-methylbutyl.

When $R_4$ is a group —$(CH_2)_sR_5$ as defined, suitable examples of $R_6$ include $C_{5-8}$ cycloalkyl, preferably cyclohexyl. s is preferably 1.

When $R_4$ is a group —$(CH_2)_tR_6$ as defined, t is preferably 1.

When $R_6$ is optionally substituted phenyl as defined above, suitable examples of such optional phenyl substituents include methyl, ethyl, n- and iso- propyl, n-, sec, and tert-butyl; methoxy, ethoxy, n- and isopropoxy; $CF_3$, fluoro, chloro or bromo. One preferred $R_6$ when optionally substituted phenyl is unsubstituted; another is 4-tolyl.

When $R_6$ is thienyl it may be 2- or 3-thienyl, generally 2-thienyl.

$R_4$ is preferably benzyl optionally substituted as hereinbefore defined, or 2-thienylmethyl, also called 2-thenyl. Optionally substituted benzyl is preferred, particularly benzyl and 4-methylbenzyl.

n is preferably 0.

X is most suitably oxygen.

Often the amide and heterogranatane nitrogen atoms, which are in the same side chain, are separated by 2 or 3, carbon atoms, most preferably 3.

In such most preferable cases the CONH(CH₂)$_n$-moiety is in an equatorial orientation to the heterogranatane ring.

The pharmaceutically acceptable salts of the compound of the formula (I) include acid addition salts with conventional acids such as hydrochloric, hydrobromic, phosphoric, sulphuric, citric, tartaric, lactic and acetic acid.

The pharmaceutically acceptable salts of the compounds of the formula (I) also include quaternary ammonium salts. Examples of such salts include such compounds quaternised by compounds such as $R_7$ - Y wherein $R_7$ is $C_{1-6}$ alkyl, phenyl-$C_{1-6}$ alkyl or $C_{5-7}$ cycloalkyl, and Y is a radical corresponding to an anion of an acid. Suitable examples of $R_7$ include methyl, ethyl and n- and iso-propyl; and benzyl and phenylethyl. Suitable examples of Y include the halides such as chloride, bromide and iodide.

Examples of pharmaceutically acceptable salts also include internal salts such as N-oxides.

The compounds of the formula (I) may also form hydrates and the invention extends to such hydrates.

A group of compounds within those of formula (I) consists of those wherein:

$R_1$ is $C_{1-6}$ alkoxy;

$R_2$ and $R_3$ are the same or different and are hydrogen, halogen, trifluoromethyl, $C_{1-7}$ acyl, $C_{1-7}$ acylamino, or amino, aminocarbonyl or aminosulphonyl optionally substituted by one or two $C_{1-6}$ alkyl groups; $C_{1-6}$ alkylsulphonyl, $C_{1-6}$ alkylsulphinyl or nitro; or $R_1$ and $R_2$ taken together are methylenedioxy or ethylenedioxy, in which case $R_3$ is any one of the groups given for $R_1$ and $R_2$ above;

$R_4$ is $C_{1-7}$ alkyl or a group —$(CH_2)_s R_5$ where s is 0 to 2 and $R_5$ is a $C_{3-8}$ cycloalkyl group, or a group —$(CH_2)_t R_6$ where t is 1 or 2 and $R_6$ is a phenyl group optionally substituted by one or two substituents selected from $C_{1-6}$ alkyl, $C_{1-6}$ alkoxy, trifluoromethyl and halogen;

X is oxygen or sulphur;

n is 0, 1 or 2; and there are at least two carbon atoms between the benzamide and side-chain nitrogen atoms.

From the aforesaid it will be seen that suitably the moiety of formula (II):

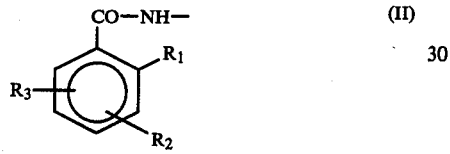
(II)

in a compound of the formula (I) will have the structure (III):

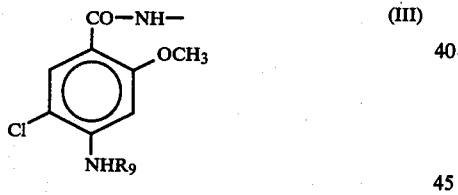
(III)

wherein $R_9$ is hydrogen or $C_{1-4}$ alkanoyl.

A preferred group of compounds within those of formula (I), are those of formula (IV), and pharmaceutically acceptable salts thereof:

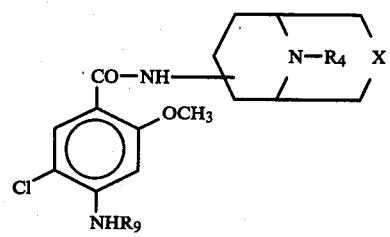
(IV)

wherein:

X, $R_4$ and $R_9$ are as defined in formulae (I) and (III).

Preferably the moiety of formula (II) is at the 7-position (standard numbering).

Suitable and preferred examples of $R_4$ in formula (IV) include those listed under formula (I) for $R_4$. Particularly preferred examples of $R_4$ include benzyl optionally substituted in the phenyl ring as defined under formula (I). Unsubstituted benzyl is an especially preferred $R_4$.

Preferably $R_9$ is hydrogen, formyl or acetyl.

A sub-group of compounds within those of formula (IV) are those of the formula (V):

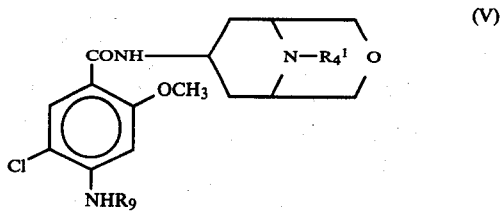
(V)

wherein $R^1_4$ is $C_{5-7}$ alkyl, and $R_9$ is as hereinbefore defined.

Suitable examples of $R^1_4$ are as so described for $R_4$ $C_{5-7}$ alkyl under formula (I). $R_9$ is preferably hydrogen, formyl or acetyl.

It is preferred that the CONH moiety is in the β-orientation to the oxagranatane ring, that is as follows:

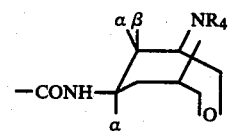

(The 6α and 6β orientations are also depicted.)

A particularly preferred sub-group of compounds within those of formula (IV) are those of the formula (VI):

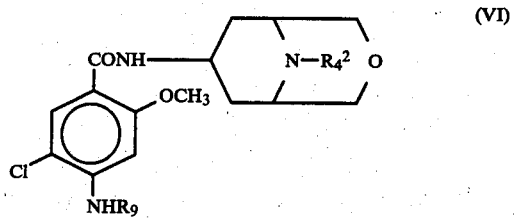
(VI)

wherein $R^2_4$ is a group —$(CH_2)_t R^1_6$ wherein t is 1 or 2 and $R^1_6$ is optionally substituted phenyl as defined in formula (I); cyclohexylmethyl; or 2-thienylmethyl, and $R_9$ is as hereinbefore defined.

Suitable and preferred $R^2_4$ are as so described for the corresponding $R_4$ groups under formula (I).

$R^2_4$ benzyl is one especially preferred value.

It is preferred that the CONH moiety is in the β-orientation to the oxagranatane ring.

A sub-group of compounds within those of the formula (IV) of interest are those of the formula (VII):

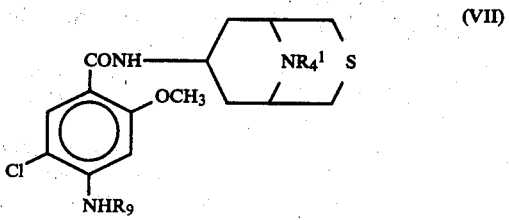
(VII)

wherein:

$R^1_4$ and $R_9$ are as defined in formula (V).

Suitable and preferred $R^1_4$ and $R_9$ are as described under formula (V).

It is preferred that the CONH moiety is in the β-orientation to the thiagranatane ring, the β-orientation being the same as in the oxagranatane hereinbefore depicted.

Another sub-group of compounds within those of the formula (IV) of interest are those of the formula (VIII):

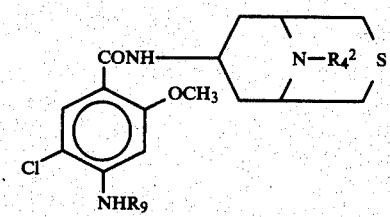
(VIII)

wherein:

$R^2_4$ and $R_9$ are as defined in formula (VI).

Suitable and preferred examples of $R^2_4$ and $R_9$ are as described under formula (VI).

It is preferred that the CONH moiety is in the β-orientation to the thiagranatane ring.

A second group of compounds within those of the formula (I) which is of interest is of the formula (IX):

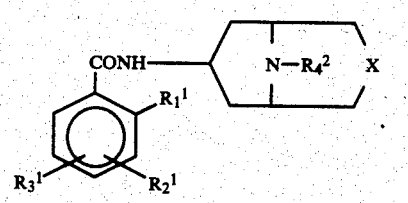
(IX)

wherein:

$R^1_1$ is $C_{1-6}$ alkoxy;

$R^1_2$ and $R^1_3$ are the same or different and are hydrogen, aminosulphonyl optionally substituted by one or two $C_{1-6}$ alkyl groups, $C_{1-6}$ alkylsulphonyl, $C_{1-6}$ alkylsulphinyl, $C_{1-6}$ alkoxy or hydroxy or $R^1_1$ and $R^1_2$ taken together are methylenedioxy or ethylenedioxy, in which case $R^1_3$ is any one of the groups given above for $R^1_2$ and $R^1_2$; and X and $R^2_4$ are as defined in formula (VI).

It is preferrred that the CONH moiety is in the β-orientation to the heterogranatane ring.

More suitably $R^1_1$ is methoxy, or together with $R^1_2$ is ethylenedioxy.

$R^1_2$ is preferably hydrogen or methoxy, and $R^1_3$ and $R^1_1$ are then preferably both methoxy.

The 2,3-dimethoxy and 2,4,5-trimethoxy nuclei (with respect to —CONH— taken as 1) are particularly preferred.

Suitable and preferred $R^2_4$ are as so described under formula (VI).

A sub-group of compounds within those of formula (IX) is of the formula (X):

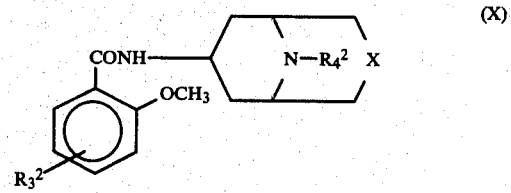
(X)

wherein:

$R^2_3$ is aminosulphonyl optionally substituted by one or two $C_{1-6}$ alkyl groups or $C_{1-6}$ alkylsulphonyl or $C_{1-6}$ alkylsulphinyl and X and $R^2_4$ are as hereinbefore defined.

$R^2_3$ is preferably aminosulphonyl or methylsulphonyl, in particular 5-aminosulphonyl or 5-methylsulphonyl (with respect to the aminocarbonyl side chain taken as 1).

Suitable and preferred $R^2_4$ are as so described under formula (VI).

A second sub-group of compounds within those of formula (IX) are those of the formula (XI):

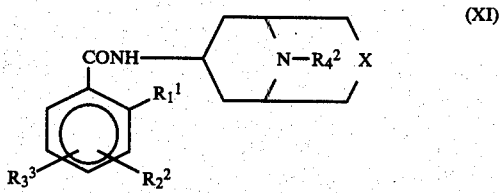
(XI)

wherein:

X, $R^1_1$ and $R^2_4$ are as defined in formula (IX);

$R^2_2$ and $R^3_3$ are the same or different and are $C_{1-6}$ alkoxy or hydrogen; or $R^1_1$ and $R^2_2$ taken together are methylenedioxy or ethylenedioxy, in which case $R^3_3$ is any one of the groups given above for $R^2_2$ and $R^3_3$.

Suitable and preferred $R^1_1$, $R^2_2$, $R^3_3$ and $R^2_4$ are as so described under formula (IX) for $R^1_1$, $R^1_2$, $R^1_3$ and $R^2_4$.

From the aforesaid it will also be seen that a third group of compounds within formula (I) of interest are those of the formula (XII):

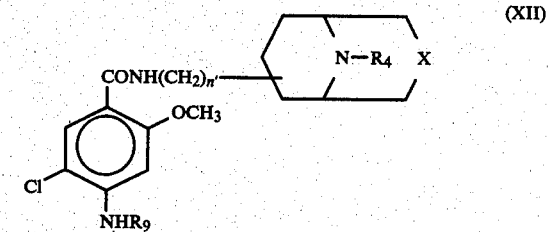
(XII)

wherein:

n' is 1 or 2 and the remaining variables are as defined in formula (I).

Preferably n is 1.

Suitable and preferred examples of $R_4$ include those listed hereinbefore for $R_4$.

A fourth group of compounds within formula (I) of interest are those of the formula (XIII):

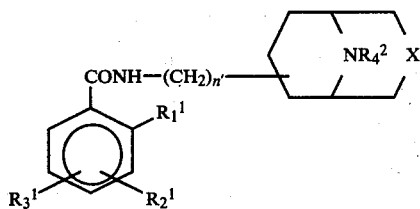

wherein:

n' is 1 or 2 and X, $R^1_1$, $R^1_2$, $R^1_3$ and $R^2_4$ are as defined in formula (IX).

Preferably n' is 1.

Suitable and preferred $R^1_1$, $R^1_2$, $R^1_3$ and $R^2_4$ are as so described under formula (IX).

Particularly suitable examples of the compounds of the present invention include those of the Examples hereinafter.

It will of course be realised that the compounds of the formula (I) have chiral or prochiral centres, and thus are capable of existing in a number of stereoisomeric forms. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The invention also provides a process for the preparation of a compound of the formula (I), which process comprises reacting an acid of the formula (XIV):

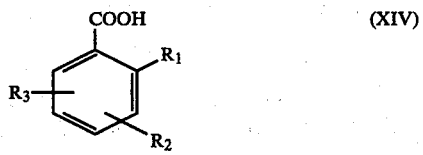

or a reactive derivative thereof, with a compound of formula (XV):

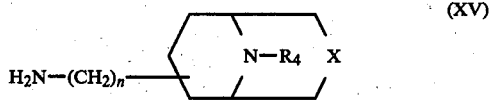

wherein:

the variable groups are as defined in formula (I); and thereafter if desired or necessary converting a group $R_2$ or $R_3$ in the thus formed compound to another group $R_2$ or $R_3$ respectively; converting $R_4$ when hydrogen to another $R_4$; and optionally forming a pharmaceutically acceptable salt of the resultant compound of the formula (I).

'Reactive derivative' when used herein means a derivative of the compound (XIV) which can be reacted with the compound (XV) to form an amido linkage between the acid group of the compound (XIV) and the amino group of the compound of the formula (XV).

Often this reactive derivative will be the acid halide, such as the acid chloride, of the acid (XIV). In such cases, the reaction will normally be carried out in an inert solvent preferably in the presence of an acid acceptor. The inert solvent can be any solvent inert to both reactants, such as benzene, toluene, diethyl ether or the like. The acid acceptor is suitably an organic base such as a tertiary amine e.g. triethylamine, trimethylamine, pyridine or picoline, or an inorganic acid acceptor, such as calcium carbonate, sodium carbonate, potassium carbonate or the like. It should also be noted that it is possible to use certain acid acceptors as the inert solvent, for example organic bases.

These reactions may be carried out at any non-extreme temperature such as $-10°-100°$ C. and more suitably $0°-80°$ C. The higher reaction temperatures are employed with less active acids of the formula (XIV) whereas the lower temperatures are employed with the more reactive acids of the formula (XIV).

Another useful reactive derivative of the acid (XIV) that may be used is a highly activated ester, such as the pentachlorophenyl ester, when ambient temperatures may be used. The reaction is generally effected in an inert polar solvent, such as dimethylformamide.

The reaction may also be carried out by forming an anhydride of the acid (XIV) in the usual manner, and reacting that with the compound (XV); normally a conventional mixed anhydride will be used; or by reacting the acid (XIV) and the compound (XV) in the presence of a dehydrating catalyst such as a carbodiimide, for example dicyclohexylcarbodiimide.

The intermediates of the formulae (XIV) and (XV) are either known compounds or can be prepared by analogous processes to known compounds.

It will be realised that in the compound of the formula (I) the $—CO—NH—(CH_2)_n—$ linkage may have an $\alpha$ or $\beta$ orientation with respect to the ring of the bicyclic moiety to which it is attached. A mixture of $\alpha$ and $\beta$ isomers of the compound of the formula (I) may be synthesised non-stereospecifically and the desired isomer separated conventionally therefrom, e.g. by chromatography; or alternatively the $\alpha$ or $\beta$ isomer may if desired be synthesized from the corresponding $\alpha$ or $\beta$ form of the compound of the formula (XV).

Synthesis from the corresponding $\alpha$ or $\beta$ isomer of compound of the formula (XV) is in general preferred.

The $\alpha$ or $\beta$ form of the compound of the formula (XV) may if desired by prepared by known stereospecific processes, such as those leading to the $\alpha$ or $\beta$ isomers of the compound of the formula (XV) depicted in the Schemes.

The precursor of the compound of the formula (XV) may be stereospecifically synthesised, such as the azide depicted in the Schemes, and then converted to the corresponding desired isomer of the compound of the formula (XV) under non-stereospecific conditions with retention of configuration. Alternatively, the precursor may itself have no asymmetric or prochiral centre at the relevant position, such as the oximes of Description 3 but be converted under stereospecific conditions to the desired isomer of the compound of the formula (XV).

Alternatively, a mixture of the $\alpha$ and $\beta$ isomers of the compound of the formula (XV) may be synthesised non-stereospecifically and the desired isomer separated conventionally therefrom e.g. by chromatography. However, in this case it is generally more convenient to react the mixture to give a mixture of $\alpha$ and $\beta$ isomers of the compound of the formula (I) and to separate these if desired as hereinbefore described.

The following Scheme 1 illustrates stereospecific and non-stereospecific synthetic routes to intermediates of the formula (XV) wherein n is 0.

It is believed that the compounds of the formula (XV) are novel and as such form an aspect of the present invention.

Scheme 1
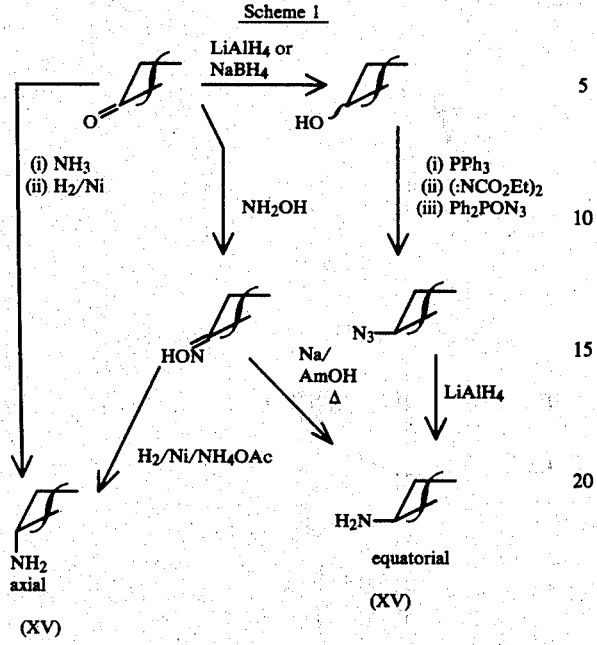
The following Scheme 2 illustrates preparative routes to intermediates of the formula (XV) wherein n is 1 or 2.
Scheme 2
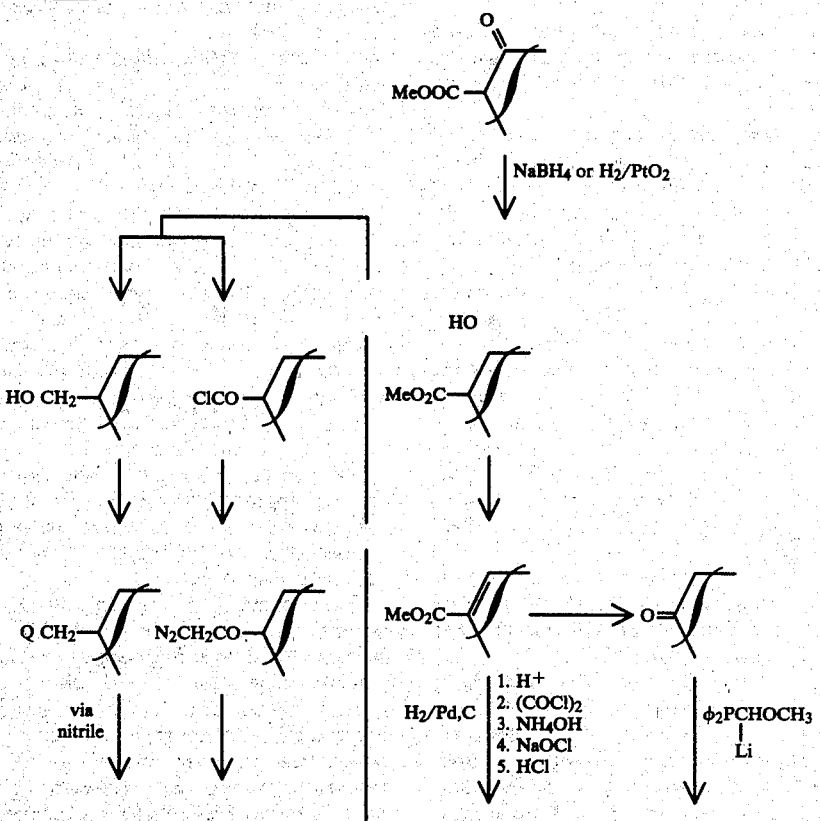

-continued
Scheme 2

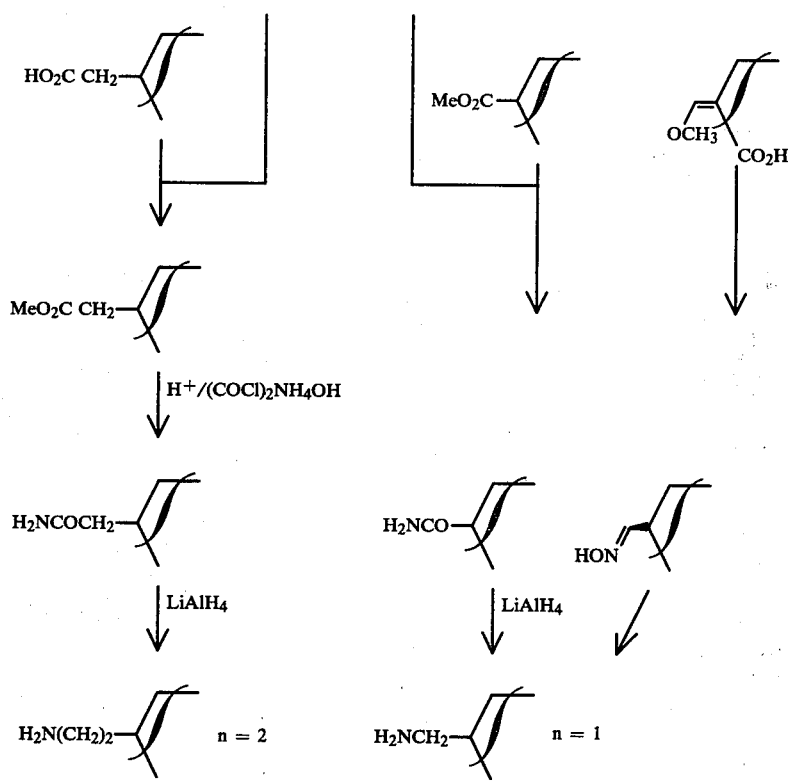

(Remainder of ring system omitted for clarity)

The acid addition salts of compounds of the formula (I) may be prepared in entirely conventional manner by reacting a compound of the formula (I) in base form with the chosen acid.

The quaternary ammonium salts of the compounds of the formula (I) may be prepared in conventional manner for such salts, such as by reaction of the chosen compound of the formula (I) with a compound $R_7Y$ as defined. This reaction is suitably carried out in an appropriate solvent such as acetone, methanol, ethanol, dimethylformamide and the like, at ambient or raised temperature and pressure.

The nitrogen atom of the heterogranatane may also form an N-oxide to give an internal N-oxide salt of the compound of the formula (I). The N-oxides may be prepared in conventional manner such as by reaction of the chosen compound of the formula (I) with an organic per-acid, such as m-chloroperbenzoic acid. This reaction is suitably carried out at below-ambient temperature in an organic solvent, preferably a chlorinated hydrocarbon solvent.

The skilled man will appreciate that the choice or necessity of conversion of groups $R_2$ and/or $R_3$ to other groups $R_2$ and/or $R_3$ will be dictated by the nature and position of substituents $R_1$, $R_2$ and $R_3$.

It will be apparent that compounds of the formula (I) containing an $R_2$, $R_3$ or $R_4$ group which is convertible to another $R_2$, $R_3$ or $R_4$ group are useful intermediates, and as such form an important aspect of the invention.

By way of example of such conversions, the compounds of the formula (I) wherein $R_2$ or $R_3$ is a nitro group may be prepared via the nitration of the corresponding intermediate product wherein $R_2$ or $R_3$ is a hydrogen atom.

A particularly suitable nitrating agent for use in this process is fuming nitric acid in the presence of sulphuric acid. In general the reagent is added to a solution of the intermediate wherein $R_2$ or $R_3$ is hydrogen, in solution in an organic solvent such as acetic acid. Normally the reaction is carried out at or below ambient temperature, for example 0°–30° C. and more suitably at about 5°–20° C., subject to the reaction medium remaining fluid.

The nitro compound may be obtained from the reaction mixture by such conventional means as neutralisation followed by extraction into a water immiscible organic solvent such as ethyl acetate or dichloromethane from which it may be recovered by evaporation. If desired the nitro compound may be purified by chromatography or by recrystallisation of the free base or an acid addition salt thereof.

An optional process step provided by this invention in the preparation of the compounds of the formula (I) wherein $R_2$ or $R_3$ is an amino group comprises the reduction of a corresponding intermediate wherein $R_2$ or $R_3$ is a nitro group.

The reduction of the intermediates wherein $R_2$ or $R_3$ is a nitro group may be effected with reagents known to be suitable for reducing nitroanisole to aminoanisole. A suitable reagent for this reduction is stannous chloride in hydrochloric acid or in mixtures of hydrochloric and acetic acid. The desired amino compound may be obtained from the reaction mixture by respectively neutralisation followed by extraction into a water immiscible solvent such as ethyl acetate from which it may be recovered by evaporation of the solvent.

Another suitable method is catalytic hydrogenation at atmospheric pressure in polar solvent such as ethanol. Transition metal catalysts such as Raney nickel are often used. The desired compound may be obtained from the reaction mixture by filtration and evaporation to dryness.

The initial crude product in both cases may be purified by chromatography or crystallisation or by forming an acid addition salt which may be recrystallised.

In general however, it is more convenient to prepare a compound of the formula (I) wherein $R_2$ or $R_3$ is an amino group from the corresponding $C_{1-7}$ acylamino acid or its reactive derivative, and to deacylate the compound of the formula (I) so formed.

Those compounds of the invention wherein $R_2$ or $R_3$ is a $C_{1-7}$ acylamino group may be prepared from the corresponding intermediate wherein $R_2$ or $R_3$ is an amino group by reaction with an acylating derivative, such as previously described as a suitable acylating derivative, e.g. of the acid of the formula (XIV). The reaction may proceed as described for the reaction of the compounds of the formula (XIV) and (XV). For an $R_2/R_3$ formamido group acylation may be effect with the free acid.

This invention thus also provides an optional process for the preparation of a compound of the formula (I) wherein $R_2$ or $R_3$ is an amino group which process comprises the deacylation of a corresponding intermediate wherein $R_2$ or $R_3$ is a $C_{1-7}$ acylamino group.

Generally the hydrolysis reaction may be effected by treatment with a base such as an alkali metal hydroxide.

Also a compound of the formula (I) wherein $R_2$ or $R_3$ is halogen may be prepared by a conventional halogenation of the corresponding intermediate wherein the said $R_2$ or $R_3$ is hydrogen.

Similarly the compounds wherein $R_2$ or $R_3$ is $C_{1-6}$ alkylthio or $C_{1-6}$ alkylsulphinyl may be oxidised to the corresponding compounds wherein $R_2$ or $R_3$ is $C_{1-6}$ alkylsulphinyl or $C_{1-6}$ alkylsulphonyl respectively.

These oxidations may conveniently be carried out conventionally at below ambient temperatures using an organic peracid in a non-aqueous inert reaction medium preferably a chlorinated hydrocarbon solvent, for example using 3-chloroperbenzoic acid, or using a water soluble inorganic strong oxidant, such as an alkali metal permanganate or hydrogen peroxide in aqueous solution.

It will be appreciated by the skilled man that, depending on the other specific substituents in the compound of the formula (I), such an oxidation on a compound of the formula (I) may also form the N-oxide of the bicyclic moiety therein.

Given the specific substitution desired and having been decided whether the compound or its N-oxide is required, the skilled man will readily ascertain whether such $R_2/R_3$ interconversion is desirable. In general it is preferred to effect the oxidation in the intermediate of formula (XIV) before coupling.

It will be appreciated that, when $R_4$ in the compound of the formula (I) is $R_5$, which is optionally substituted benzyl as hereinbefore defined, $R_4$ may be replaced by another group $R_4$.

Such $R_5$ benzyl groups may be removed for example when $R_2$ or $R_3$ is not halogen by conventional transition metal catalysed hydrogenolysis to give compounds of the formula (XVI):

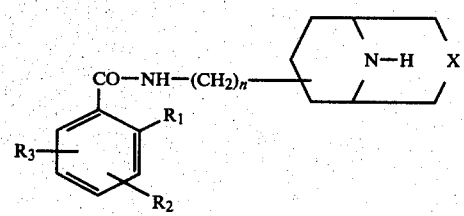

wherein the variable groups are as defined in formula (I).

This invention also provides an optional process step in the preparation of a compound of the formula (I) which comprises the reaction of a corresponding compound of the formula (XVI) as hereinbefore defined with a compound $QR_4$ wherein $R_4$ is as defined in formula (I) and Q is a group or atom readily displaced by a nucleophile, and optionally forming a pharmaceutically acceptable salt of the resulting compound of the formula (I).

Suitable values for Q include Cl, Br, I, $OSO_2CH_3$ or $OSO_2C_6H_4pCH_3$.

Favoured values for Q include Cl, Br and I.

Particularly suitably the compound $QR_4$ is a benzyl halide such as benzyl bromide or benzyl chloride.

The reaction may be carried out under conventional alkylation conditions for example in an inert solvent such as dimethylformamide in the presence of an acid acceptor such as potassium carbonate. Generally the reaction is carried out at a non-extreme temperature such as at ambient or at a slightly elevated temperature.

However, it is generally more convenient to interconvert $R_4$ in the compound of the formula (XV) before coupling with the compound of the formula (XIV) or its derivative. Such interconversions are effected conveniently under the above conditions. It is desirable to protect the amine function with a group readily removeable by acidolysis such as a $C_{2-7}$ alkanoyl group before $R_4$ interconversion.

It will be appreciated that, when $R_2$ or $R_3$ are converted to other $R_2$ or $R_3$ and $R_8$ being hydrogen is converted to $R_4$, then these conversions may take place in any desired or necessary order.

As hereinbefore stated, the compounds of the formula (I) are dopamine antagonists.

Depending on their balance between peripheral and central action, the compounds of the formula (I) may be used in the treatment of disorders related to impaired gastro-intestinal motility, such as retarded gastric emptying, dyspepsia, flatulence, oesophagal reflux, peptic ulcer and emesis, and/or in the treatment of disorders of the central nervous system, such as psychosis.

All the compounds of the formula (I) may be used in the treatment of emesis.

Examples of compounds of the formula (I) which are of particular interest for their CNS activity, in particular anti-pyschotic activity, are those wherein $R_4$ is $R^1_4$ or $R^2_4$ as defined, preferably $R^2_4$, in particular optionally substituted benzyl.

Examples of compounds of more interest for their beneficial effect on gastric motility are the quaternary ammonium salts of the compounds of the formula (I).

The invention also provides a pharmaceutical composition comprising a compound of the formula (I), or a hydrate or a pharmaceutically acceptable salt thereof, together with a pharmaceutically acceptable carrier.

Such compositions may be adapted for oral or parenteral administration, and as such may be in the form of tablets, capsules, oral liquid preparations, powders, granules, lozenges, reconstitutable powders, injectable and infusable solutions or suspensions and the like; the compositions may also be in the form of suppositories and the like. Normally, orally administrable compositions are preferred.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented in a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration. fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention further provides a method of treatment of maladies in humans comprising the administration of an effective amount of a compound of the formula (I) or a pharmaceutically acceptable salt thereof. The "effective amount" will depend in the usual way on a number of factors such as the nature and severity of the malady to be treated, the weight of the sufferer, and the actual compound used.

However by way of illustration, unit doses will suitably contain 0.1 to 20 mgs of the compound of formula (I), for example 0.5 to 10 mgs.

Again by way of illustration, such unit doses will suitably be administered more than one a day, for example 2, 3, 4, 5 or 6 times a day, in such a way that the total daily dose is suitably in the range 0.01 to 10 mg/kg per day.

Compounds of the formula (I) have the ability to potentiate the effect of conventional analgesics in migraine treatment when administered concurrently with the analgesic.

Thus the invention provides a pharmaceutical composition comprising a compound of the formula (I) and an analgesic.

The compound of the formula (I) and the analgesic, such as aspirin or paracetamol, will be present in the composition in amounts generally similar to their usual effective dose.

The composition can be a combination product, for example a tablet or capsule containing both a compound of the formula (I) and an analgesic for oral administration, or a twin pack comprising the two active ingredients made up for separate administration.

The invention accordingly provides a method of treatment of migraine comprising the administration to the sufferer of a compound of the formula (I) and an analgesic.

The following Examples illustrate the preparation of the compounds of formula (I) and the following Descriptions illustrate the preparation of intermediates thereto.

DESCRIPTION 1A

9-Benzyl-9-aza-3-oxabicyclo(3,3,1)-nonan-7-one (D1)

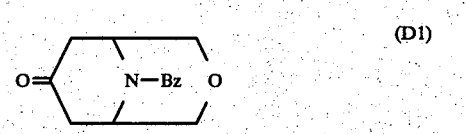

Oxydiacetaldehyde bis dimethylacetal (11.7 g, 60.3 mmole) was stirred and refluxed with a solution of 3 ml glacial acetic acid and 12 ml water for a period of 2 hours. This was then allowed to cool and the solution was diluted with 150 ml of a buffer solution made from citric acid/disodium hydrogen phosphate. A solution of benzylamine hydrochloride (made from 11.9 ml benzylamine and 9 ml concentrated hydrochloric acid) was then added followed by portionwise addition of acetone dicarboxylic acid (17.55 g, 120 mmole). The pH of the resulting solution was adjusted to 4, and this was allowed to stir for 36 hours with occasional addition of citric acid to maintain the pH.

At the end of this period the solution was made strongly acidic with hydrochloric acid and this was extracted with several portions of ether (which were discarded). The solution was then basified with aqueous sodium hydroxide and extracted with dichloromethane (4×300 ml). Evaporation of the organic extracts gave a brown oil sludge which was recrystallized from dichloromethane to give the desired ketone as an off-white solid (2.55 g, 18%).

DESCRIPTION 1B

9-Benzyl-9-aza-3-thiabicyclo(3,3,1)nonan-7-one (D2)

Thiadiacetaldehyde bis-dimethylacetal (23.1 g) was refluxed with 1.5% dilute hydrochloric acid (75 ml) for 2 hours and cooled. To this was added a solution of benzylamine (13.25 ml) and concentrated hydrochloric acid (11 ml) in water (250 ml) followed by acetone dicarboxylic acid (19.2 g). The mixture was made up to 1 liter with water and the pH adjusted to 2.5. After stirring for 24 hours it was acidified with concentrated hydrochloric acid and saturated with several portions of diethyl ether. The aqueous solution was then basified and extracted with dichloromethane (6×250 ml). The solution was evaporated and absorbed on alumina (100 g) and this was then placed in the thimble of a soxhlet extraction apparatus. This was then continually extracted with ether for 48 hours. Recrystallization gave the desired 9-benzyl-9-aza-3-thiabicyclo[3,3,1]nonan-7-one as a white solid (8.3 g; 30%).

DESCRIPTION 2

9-Benzyl-9-aza-3-oxabicyclo-(3,3,1)-nonan-7-one oxime (D3)

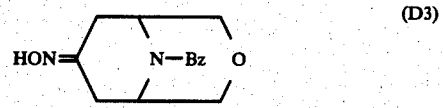

The ketone (D1) from the previous reaction (0.96 g) was dissolved in ethanol (60 ml) together with hydroxylamine hydrochloride (0.29 g) and pyridine (0.4 ml). This mixture was refluxed with stirring overnight, then poured into water and basified by the addition of solid potassium carbonate. The mixture was extracted with chloroform (4×250 ml), and the combined organic extracts were dried (over sodium sulphate) and evaporated to yield the crude oxime (quantitative).

The following compound was prepared analogously:
9-benzyl-9-aza-3-thiabicyclo[3.3.1]nonan-7-one oxime (D4) (crude quantitative yield) from (D2).

DESCRIPTION 3

7β-Amino-9-benzyl-9-aza-3-oxabicyclo(3,3,1)nonane (D5)

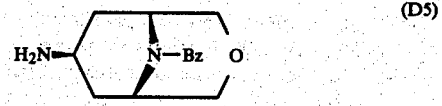

The oxime (D3) from the previous reaction (2 g) was dissolved with stirring in amylalcohol (150 ml) and this was heated to 140° C. Sodium (6 g) was added in small pieces over a period of 40 minutes and when addition was complete, the solution was refluxed for a further 5 hours, then allowed to cool. The cold solution was poured into water and made strongly acidic by the addition of hydrochloric acid. This was then extracted with ethyl acetate (6×200 ml). The aqueous solution was basified with sodium hydroxide saturated with sodium chloride and then extracted with chloroform (4×200 ml). Drying (over sodium sulphate) followed by evaporation of the solvent gave a quantitative yield of the crude amine as a yellow oil which solidified on standing.

The following compound was prepared analogously:
7β-amino-9-benzyl-9-aza-3-thiabicyclo[3.3.1]nonane (D6) (98% yield) from (D4).

DESCRIPTION 4

7β-Acetamido-9-benzyl-9-aza-3-oxabicyclo(3,3,1)nonane (D7)

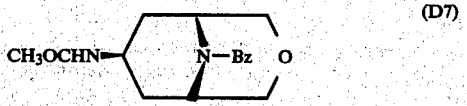

The amine (D5) (19.5 g) from Description 3 was dissolved in 250 ml of ethanol together with a large excess of acetic anhydride. This mixture was stirred at ambient temperature for 2 days. The solvent was evaporated, aqueous sodium carbonate solution added and the solution extracted with methylene chloride (3×200 ml). Drying (over magnesium sulphate) followed by evaporation of the solvent gave the crude product (20.8 g, 92%).

DESCRIPTION 5

7β-Acetamido-9-aza-3-oxabicyclo(3,3,1)none (D8)

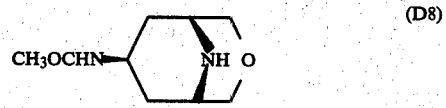

The product (D7) from Description 4 (5 g) was dissolved in 250 ml of ethanol and hydrogenated with 10% palladium/charcoal at atmospheric pressure and ambient temperature. The solution was filtered and solvent evaporated to give a quantitative yield of the crude amine as an oil which solidified on standing.

DESCRIPTION 6

7β-Acetamido-9-(4-chlorobenzyl)-9-aza-3-oxabicyclo(3,3,1)nonane (D9)

The amine (1 g, 5.3 mmol) from Description 8 and p-chlorobenzyl chloride (0.87 g, 5.3 mmol) were dissolved in 40 ml of dry dimethylformamide and potassium carbonate (2.2 g) added. The mixture was stirred at ambient temperature for 2 days. The solvent was evaporated, water was added and the solution extracted with methylene chloride (3×100 ml). Drying (over magnesium sulphate) followed by evaporation of the solvent gave the product (1.33 g; 81%).

Similarly prepared were:
7β-Acetamido-9-(4-methoxybenzyl)-9-aza-3-oxabicyclo (3,3,1)nonane (D10)
7β-Acetamido-9-(3,4-dichlorobenzyl)-9-aza-3-oxabicyclo(3,3,1)nonane (D11)
7β-Acetamido-9-(3-trifluoromethylbenzyl)-9-aza-3-oxabicyclo(3,3,1)nonane (D12)
7β-Acetamido-9-(4-methylbenzyl)-9-aza-3-oxabicyclo (3,3,1)nonane (D13)
7β-Acetamido-9-(n-hexyl)-9-aza-3-oxabicyclo(3,3,1)nonane (D14)
7β-Acetamido-9-(2-thenyl)-9-aza-3-oxabicyclo(3,3,1-)nonane (D15)
7β-Acetamido-9-(3-methylbutyl)-9-aza-3-oxabicyclo (3,3,1)nonane (D16)
7β-Acetamido-9-(cyclohexylmethyl)-9-aza-3-oxabicyclo (3,3,1)nonane (D17)
7β-Acetamido-9-(4-methylpentyl)-9-aza-3-oxabicyclo (3,3,1)nonane (D18)
7β-Acetamido-9-(n-heptyl)-9-aza-3-oxabicyclo(3,3,1-)nonane (D19).

DESCRIPTION 7

7β-Amino-9-(4-chlorobenzyl)-9-aza-3-oxabicyclo(3,3,1-)nonane (D18)

The product from Description 9 (1.33 g, 4.3 mmole) was dissolved in 20 ml of ethanol and 20 ml of concentrated hydrochloric acid. The solution was refluxed for 8 hours, allowed to cool and the ethanol evaporated.

The aqueous solution was washed with ethyl acetate, made basic with potassium carbonate and extracted with methylene chloride (4×100 ml). Drying (over magnesium sulphate) followed by evaporation of the solvent gave the amine as a yellow oil (0.63 g; 55%).

Similarly prepared were:
7β-Amino-9-(4-methoxybenzyl)-9-aza-3-oxabicyclo(3,3,1)nonane (D19)
7β-Amino-9-(3,4-dichlorobenzyl)-9-aza-3-oxabicyclo(3,3,1)nonane (D20)
7β-Amino-9-(3-trifluoromethylbenzyl)-9-aza-3-oxabicyclo(3,3,1)nonane (D21)
7β-Amino-9-(4-methylbenzyl)-9-aza-3-oxabicyclo(3,3,1)nonane (D22)
7β-Amino-9-(n-hexyl)-9-aza-3-oxabicyclo(3,3,1)nonane (D23)
7β-Amino-9-(2-thenyl)-9-aza-3-oxabicyclo(3,3,1)nonane (D24)
7β-Amino-9-(3-methylbutyl)-9-aza-3-oxabicyclo(3,3,1)nonane (D25)
7β-Amino-9-(cyclohexylmethyl)-9-aza-3-oxabicyclo(3,3,1)nonane (D26)
7β-Amino-9-(4-methylpentyl)-9-aza-3-oxabicyclo(3,3,1)nonane (D27)
7β-Amino-9-(n-heptyl)-9-aza-3-oxabicyclo(3,3,1)nonane (D28)

EXAMPLE 1

2-Methoxy-5-chloro-4-acetamido-N-[9-benzyl-9-aza-3-oxabicyclo(3,3,1)nonan-7β-yl]-benzamide (1)

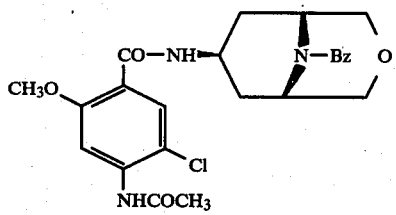

2-Methoxy-5-chloro-4-acetamido-benzoic acid (2.47 g, 10.1 mmol) was converted to its acyl chloride by treatment with 20 ml thionyl chloride at 40° C. for 4 hours, followed by removal of the excess thionyl chloride. This was then dissolved in dry toluene (150 ml) and 4 ml of triethylamine was added. A solution of the amine (2.14 g, 9.2 mmol) from the previous description in dry toluene (50 ml) was added and the solution was allowed to sit at ambient temperature for 2 days. Chloroform (200 ml) was then added and the solution was washed with aqueous potassium carbonate solution, dried (over sodium sulphate) and evaporated. The oil was then redissolved in chloroform/ethyl acetate, filtered and chromatographed on 5% deactivated neutral alumina). The yield of final material was 3.46 g (82%). m.pt. 186°-7° C. (from chloroform/ethyl acetate).

The following compound was prepared analogously:
2-methoxy-5-chloro-4-acetamido-N-(9-benzyl-9-aza-3thiabicyclo[3.3.1]nonan-7β-yl)benzamide (3) (52% yield, mp. 179°-181° C.).

EXAMPLE 2

2-Methoxy-5-chloro-4-amino-N-[9-benzyl-9-aza-3-oxabicyclo(3,3,1)nonan-7β-yl]-benzamide (2)

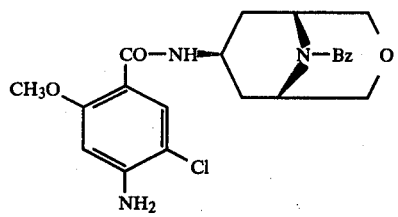

The benzamide of Example 1 (1.85 g, 4 mmol) was dissolved in 50 ml ethanol containing 3 ml water and 2 g potassium hydroxide. This was refluxed on a steam bath for 1½ hours, poured into water and saturated with sodium chloride. The aqueous solution was extracted with chloroform (6×200 ml) and the combined organic layers were dried (sodium sulphate) filtered and evaporated to yield the crude desired benzamide, (1.5 g, 90%). This was recrystallised from chloroform/ethanol/ethyl acetate to yield 1.1 g pale yellow crystals. m.pt. 255°-7° C.

The following compound was prepared analogously:
2-methoxy-5-chloro-4-amino-N-(9-benzyl-9-aza-3-thiabicyclo[3.3.1]nonan-7β-yl)benzamide (4) (66% yield, mp 263°-4° C.) from (3).

EXAMPLE 3

2-Methoxy-5-methylsulphonyl-N-[9-benzyl-9-aza-3-thiabicyclo (3,3,1)nonan-7β-yl]benzamide (5)

2-methoxy-5-methylsulphonylbenzoic acid (1.47 g) was dissolved in dimethylformamide containing triethylamine (0.65 g) and to this was added ethyl chloroformate (0.7 g). The mixture was stirred for 2 hours then 7β-amino-9-benzyl-9-aza-3-thiabicyclo(3,3,1)nonane (D6) (1.44 g) was added. These were stirred together for 48 hours and then the dimethylformamide was stripped off in vacuo and the mixture poured into aqueous potassium carbonate solution. This was extracted with chloroform, dried (sodium sulphate) filtered and evaporated to give the crude product (2.5 g). Purification by chromatography on deactivated neutral alumina gave the desired 2-methoxy-5-methylsulphonyl-N-[9-benzyl-9-aza-3-thiabicyclo(3,3,1)nonan-7β-yl]benzamide (1.87 g; 70%; mp. 197°-9° C.

EXAMPLE 4

2,3-Dimethoxyj-[N-(9-benzyl-9-aza-3-oxabicyclo(3,3,1)nonan-7β-yl)]benzamide (6)

2,3-Dimethoxybenzoic acid (1.18 g; 6.5 mmol) was converted to its acyl chloride by treatment with 20 ml thionyl chloride at 40° C. for 4 hours, followed by removal of the excess thionyl chloride. A solution of the amine (1.5 g, 6.5 mmol) (D7) in dry toluene (50 ml) was added, followed by 2 ml of triethylamine, and the solution stirred at ambient temperature for 24 hours. The solvent was evaporated, aqueous sodium carbonate solution added and the solution extracted with methylene chloride (3×50 ml). The combined organic extracts were dried (over magnesium sulphate) and evaporated. The oil was then chromatographed on silica gel. The yield of final material was 1.1 g (43%) mp. 140°-2° C. (from ethyl acetate/ether).

Similarly prepared was:

2,4,5-Trimethoxy-[N-(9-benzyl-9-aza-Lb 3-oxabicyclo(3,3,1)nonan-7β-yl)benzamide. Yield 0.4 g; (20%) mp. 125°-8° C.

EXAMPLE 5

2-Methoxy-5-chloro-4-acetamido-[N-(9-(4'-chlorobenzyl)9-aza-3-oxabicyclo(3,3,1)nonan-7β-yl)]benzamide (8)

2-Methoxy-5-chloro-4-acetamidobenzoic acid (0.73 g, 3.0 mmol) was converted to its acyl chloride by treatment with 20 ml thionyl chloride at 40° C. for 4 hours, followed by removal of the excess thionyl chloride. A solution of the amine (0.81 g, 3.0 mmol) (D7) in dry toluene (50 ml) was added, followed by 2 ml of triethylamine, and the solution was stirred at ambient temperature for 24 hours. The solvent was evaporated, aqueous sodium carbonate solution added and the solution extracted with methyline chloride (3×50 ml). Drying (over magnesium sulphate) followed by evaporation of the solvent gave an oil which was chromatographed on silica gel. The yield of final material was 1.0 g (68%).

Similarly prepared were:

2-Methoxy-5-chloro-4-acetamido-[N-(9-(3',4'-dichlorobenzyl)-9-aza-3-oxabicyclo[3.3.1]nonan-7β-yl)]benzamide (9)

2-Methoxy-5-chloro-4-acetamido-[N-(9-(3'-trifluoromethylbenzyl)-9-aza-3-oxabicyclo[3.3.1]nonan-7β-yl)]benzamide (10)

2-Methoxy-5-chloro-4-acetamido-[N-(9-(4'-methylbenzyl)9-aza-3-oxabicyclo[3.3.1]nonan-7β-yl)]benzamide (11)

2-Methoxy-5-chloro-4-acetamido-[N-(9-(n-hexyl)-9-aza-3-oxabicyclo[3.3.1]nonan-7β-yl)]benzamide (12)

2-Methoxy-5-chloro-4-acetamido-[N-(9-(2'-thenyl)-9-aza-3-oxabicyclo[3.3.1]nonan-7β-yl)]benzamide (13)

2-Methoxy-5-chloro-4-acetaido-[N-(9-(3'-methylbutyl)9-aza-3-oxabicyclo[3.3.1]nonan-7β-yl)]benzamide (14)

2-Methoxy-5-chloro-4-acetamido-[N-(9-(cyclohexylmethyl)9-aza-3-oxabicyclo[3.3.1]nonan-7β-yl)]benzamide (15)

2-Methoxy-5-chloro-4-acetamido-[N-(9-(4-methylpentyl)9-aza-3-oxabicyclo[3.3.1]nonan-7β-yl)]benzamide (16)

2-Methoxy-5-chloro-4-acetamido-[N-(9-(n-heptyl)9-aza-3-oxabicyclo[3.3.1]nonan-7β-yl)]benzamide (7)

EXAMPLE 6

2-Methoxy-5-chloro-4-amino-[N-(9-(4-chlorobenzyl)-9-aza-3-oxabicyclo(3,3,1)nonan-7β-yl)]benzamide (18)

The benzamide (8) (1.0 g, 2.0 mmol) was dissolved in 50 ml ethanol containing 3 ml water and 1 g potassium hydroxide. This was refluxed for 2 hours, allowed to cool and the solvent evaporated. Aqueous sodium carbonate solution was added and the solution extracted with methlene chloride (4×100 ml). Drying (over magnesium sulphate) followed by evaporation of the solvent gave the crude desired benzamide (0.72 g). This was recrystallised from ethanol to yield 0.57 g (63%) pale yellow crystals mpt 240°-2° C.

Similarly prepared were:

2-Methoxy-5-chloro-4-amino-[N-(9-(4-methoxybenzyl)9-aza-3-oxabicyclo(3,3,1)nonan-7β-yl)]benzamide (19)

Yield: 0.3 g, (47%) mp. 215°-17° C.

2-Methoxy-5-chloro-4-amino-[N-(9-(3,4-dichlorobenzyl)-9-aza-3-oxabicyclo(3,3,1)nonan-7β-yl)]benzamide (20)

Yield: 0.4 g, (50%) mp. 221°-3° C.

2-Methoxy-5-chloro-4-amino-[N-(9-(3-trifluoromethylbenzyl)-9-aza-3-oxabicyclo(3,3,1)nonan-7β-yl)]benzamide (21)

Yield: 0.6 g, (44%) mp. 217°-9° C.

2-Methoxy-5-chloro-4-amino-[N-(9-(4-methylbenzyl)-9-aza-3-oxabicyclo(3,3,1)nonan-7β-yl)]benzamide (22)

Yield: 0.6 g, (44%) mp. 223°-5° C.

2-Methoxy-5-chloro-4-amino[N-(9-(n-hexyl)-9-aza-3-oxabicyclo(3,3,1)nonan-7β-yl)]benzamide (23)

Yield: 0.4 g, (41%) mp. 173°-5° C.

2-Methoxy-5-chloro-4-amino-[N-(9-(2-thenyl)-9-aza-3-oxabicyclo(3,3,1)nonan-7β-yl)]benzamide (24)

Yield: 0.6 g, (42%) mp. 228°-30° C.

2-Methoxy-5-chloro-4-amino-[N-(9-(3-methylbutyl)-9-aza-3-oxabicyclo(3,3,1)nonan-7β-yl)]benzamide (25)

Yield: 0.3 g, (33%) mp. 231°-2° C.

2-Methoxy-5-chloro-4-amino-[N-(9-cyclohexylmethyl)-9-aza-3-oxabicyclo(3,3,1)nonan-7β-yl)]benzamide (26)

Yield: 0.3 g, (55%) as a foam.

2-Methoxy-5-chloro-4-amino-[N-(4-methylpentyl)-9-aza-3-oxabicyclo(3,3,1)nonan-7β-yl)]benzamide (27)

2-Methoxy-5-chloro-4-amino-[N-(n-heptyl)-9-aza-3-oxabicyclo(3,3,1)nonan-7β-yl)]benzamide (28).

PHARMACOLOGICAL DATA

I. Anti-emetic activity in the dog

Compounds were administered subcutaneously 30 minutes prior to administration of a standard dose of apomorphine HCl (0.1 mg/kg subcutaneously) and the vomiting response compared to that obtained when the same animals were dosed with apomorphine HCl and vehicle only.

The following results were obtained:

| Compound Number | $ED_{50}$ (mg/kg s.c.) |
|---|---|
| 2 | 0.005 |
| 5 | 0.1 |

II. Dopamine Receptor Blocking Activity in the Central Nervous System

Compounds were tested for inhibition of apomorphine induced climbing in the mouse. The test is based on that described by Protais, P., Constantin, J. and Schwartz J. C. (1976), Psychopharmacology, 50, 1–6.

Apomorphine 1 mg/kg s.c. induces mice to climb the wall of a wire cage (inverted food hopper-11×7.5×18 cm high). Mice acclimatised in their home cages in groups of 5 are placed under the hoppers immediately after the injection of apomorphine 1 mg/kg s.c. At 10, 20 and 30 minutes after injection climbing behaviour is scored. The mice are observed for 30 seconds and scored according to the position they spend the majority of time in, score 0—four paws on floor of cage; score 1—four paws only on walls; score 2—all paws on wall of cage. The scores at all 3 times and for each mouse are summed and mice drug treated orally compared to mice receiving apomorphine only. A saline only treated group is also included and any score, generally <5% of maximum taken into account.

The following results were obtained:

| Compound Number | Active Dose (mg/kg) |
|---|---|
| | p.o. |
| 1 | 2 |
| 2 | 1 |
| 3 | $ED_{50}$ —1.5 |
| 4 | $ED_{50}$ —3.7 |
| 5 | 50 (s.c.) |
| 6 | 2 |
| 7 | 10 |
| 18 | 10 |
| 19 | 10 |
| 20 | 10 |
| 21 | 50 |
| 22 | 10 |
| 23 | 10 |
| 24 | 10 |
| 25 | 10 |
| 26 | 10 |

It should be noted that these doses (except where $ED_{50}$'s are quoted) are not necessarily the lowest active doses.

III. Gastric Motility Testing in the rat

The compounds were tested for ability to reverse the inhibitory effect of 6,7-ADTN on gastric motility as recorded by an open tipped catheter in the conscious chronic gastric fistula rat. Administration of 1 mg/kg s.c. of 6,7-ADTN reduced basal gastric motor activity and this was reversed by the administration of the compound administered 10 minutes after the 6,7-ADTN. Control injections did not reverse the inhibition. For subcutaneous testing the compound was dissolved in water by the addition of tartaric acid (½ mole per mole of compound).

Compounds 2 and 5 both reversed the action of 6,7-ADTN at 1 mg/kg s.c.

What we claim is:

1. A compound of the formula (I) or a pharmaceutically acceptable salt thereof:

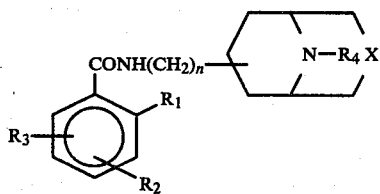

(I)

characterised in that:
X is oxygen or sulphur;
$R_1$ is a $C_{1-6}$ alkoxy or $C_{1-6}$ alkylthio group;
$R_2$ and $R_3$ are the same or different and are hydrogen, halogen, $CF_3$, $C_{1-7}$acyl, $C_{1-7}$ acylamino or amino, aminocarbonyl or aminosulphonyl optionally substituted by one or two $C_{1-6}$ alkyl groups, $C_{1-6}$ alkylsulphonyl, $C_{1-6}$ alkylsulphinyl, $C_{1-6}$alkoxy, $C_{1-6}$ alkylthio, hydroxy or nitro or $R_1$ and $R_2$ taken together are methylenedioxy or ethylenedioxy in which case $R_3$ is any one of the groups given for $R_2$ and $R_3$ above;
$R_4$ is $C_{1-7}$ alkyl or a group —$(CH_2)_sR_5$ where s is 0 to 2 and $R_5$ is a $C_{3-8}$ cycloalkyl group, or a group —$(CH_2)_tR_6$ where t is 1 or 2 and $R_6$ is a phenyl group optionally substituted by one or two substituents selected from $C_{1-6}$ alkyl, $C_{1-4}$alkoxy, trifluoromethyl and halogen, or a thienyl group; and n is 0 to 2;
and there are at least two carbon atoms between the benzamide and heterogranatane ring nitrogen atoms.

2. A compound according to claim 1 or a pharmaceutically acceptable salt thereof characterised in that:
$R_1$ is $C_{1-6}$ alkoxy;
$R_2$ and $R_3$ are the same or different and are hydrogen, halogen, trifluoromethyl, $C_{1-7}$ acyl, $C_{1-7}$ acylamino, or amino, aminocarbonyl or aminosulphonyl optionally substituted by one or two $C_{1-6}$ alkyl groups; $C_{1-6}$ alkylsulphonyl, $C_{1-6}$ alkylsulphinyl or nitro; or
$R_1$ and $R_2$ taken together are methylenedioxy or ethylenedioxy, in which case $R_3$ is any one of the groups given for $R_1$ and $R_2$ above;
$R_4$ is $C_{1-7}$ alkyl or a group —$(CH_2)_sR_5$ where s is 0 to 2 and $R_5$ is a $C_{3-8}$ cycloalkyl group, or a group —$(CH_2)_tR_6$ where t is 1 or 2 and $R_6$ is a phenyl group optionally substituted by one or two substituents selected from $C_{1-6}$ alkyl, $C_{1-6}$ alkoxy, trifluoromethyl and halogen;
X is oxygen or sulphur;
n is 0, 1 or 2; and there are at least two carbon atoms between the benzamide and side-chain nitrogen atoms.

3. A compound according to claim 1 having the formula (IV) or a pharmaceutically acceptable salt thereof:

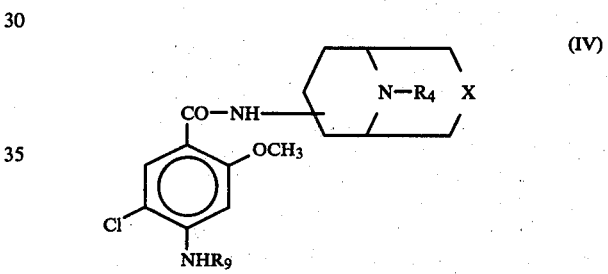

(IV)

characterised in that:
X and $R_4$ are as defined in claim 1, and $R_9$ in hydrogen or $C_{1-7}$ alkanoyl.

4. A compound according to claim 3 having the formula (V) or a pharmaceutically acceptable salt thereof:

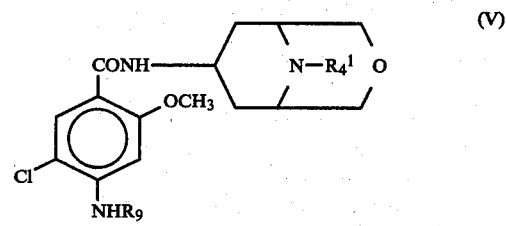

(V)

wherein:
$R^1_4$ is $C_{5-7}$ alkyl, and $R_9$ is as defined in claim 3.

5. 2-Methoxy-5-chloro-4-amino-N-(9-n-hexyl-9-aza-3-oxabicyclo[3.3.1]non-7β-yl)benzamide,
2-Methoxy-5-chloro-4-amino-N-[9-(3'-methylbutyl)-9-aza-3-oxabicyclo[3.3.1]non-7β-yl)benzamide,
2-Methoxy-5-chloro-4-acetamido-N-(9-n-hexyl-9-aza-3-oxabicyclo[3.3.1]non-7β-yl)benzamide, or
2-Methoxy-5-chloro-4-amino-N-[9-(3'-methylbutyl)-9-aza-3-oxabicyclo[3.3.1]non-7β-yl)benzamide, or a pharmaceutically acceptable salt thereof.

6. A compound according to claim 3 having the formula (VI):

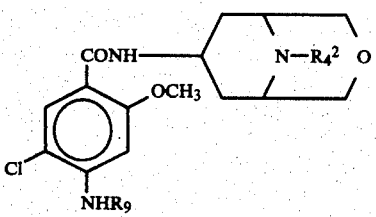

wherein:
$R^2_4$ is a group —$(CH_2)_tR^1$ wherein t is 1 or 2 and $R^1_6$ is optionally substituted phenyl as defined in formula (I); cyclohexylmethyl; or 2-thienylmethyl, and $R_9$ is as defined in claim 3.

7. 2-Methoxy-5-chloro-4-amino-N-(9-benzyl-9-aza-3-oxabicyclo[3.3.1]non-7β-yl)benzamide,
2-Methoxy-5-chloro-4-amino-N-[9-(4'-chlorobenzyl)-9-aza-3-oxabicyclo[3.3.1]non-7β-yl]benzamide,
2-Methoxy-5-chloro-4-amino-N-[9-(3',4'-dichlorobenzyl)-9-aza-3-oxabicyclo[3.3.1]non-7β-yl]benzamide,
2-Methoxy-5-chloro-4-amino-N-[9-(3'-trifluoromethylbenzyl)-9-aza-3-oxabicyclo[3.3.1]non-7β-yl]benzamide,
2-Methoxy-5-chloro-4-amino-N-[9-(4'-methylbenzyl)-9-aza-3-oxabicyclo[3.3.1]non-7β-yl]benzamide,
2-Methoxy-5-chloro-4-amino-N-[9-(2'-thenyl)-9-aza-3-oxabicyclo[3.3.1]non-7β-yl]benzamide,
2-Methoxy-5-chloro-4-amino-N-[9-(cyclohexylmethyl)-9-aza-3-oxabicyclo[3.3.1]non-7β-yl]benzamide,
2-Methoxy-5-chloro-4-acetamido-N-(9-benzyl-9-aza-3-oxabicyclo[3.3.1]non-7β-yl)benzamide,
2-Methoxy-5-chloro-4-acetamido-N-[9-(4'-chlorobenzyl)-9-aza-3-oxabicyclo[3.3.1]non-7β-yl]benzamide,
2-Methoxy-5-chloro-4-acetamido-N-[9-(3',4'-dichlorobenzyl)-9-aza-3-oxabicyclo[3.3.1]non-7β-yl]benzamide,
2-Methoxy-5-chloro-4-acetamido-N-[9-(3'-trifluoromethylbenzyl)-9-aza-3-oxabicyclo[3.3.1]non-7β-yl]benzamide,
2-Methoxy-5-chloro-4-acetamido-N-[9-(4'-methylbenzyl)-9-aza-3-oxabicyclo[3.3.1]non-7β-yl]benzamide,
2-Methoxy-5-chloro-4-acetamido-N-[9-(2'-thenyl)-9-aza-3-oxabicyclo[3.3.1]non-7β-yl]benzamide, or
2-Methoxy-5-chloro-4-acetamido-[9-(cyclohexylmethyl)-9-aza-3-oxabicyclo[3.3.1]non-7β-yl]benzamide, or a pharmaceutically acceptable salt thereof.

8. A compound according to claim 1 having the formula (IX) or a pharmaceutically acceptable salt thereof:

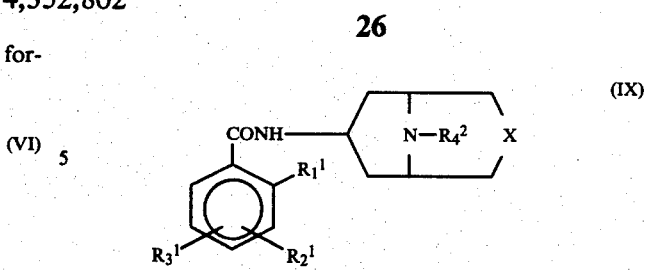

wherein:
$R^1_1$ is $C_{1-6}$ alkoxy;
$R^1_2$ and $R^1_3$ are the same or different and are hydrogen, aminosulphonyl optionally substituted by one or two $C_{1-6}$ alkyl groups, $C_{1-6}$ alkylsulphonyl, $C_{1-6}$ alkylsulphinyl, $C_{1-6}$ alkoxy or hydroxy or
$R^1_1$ and $R^1_2$ taken together are methylenedioxy or ethylenedioxy, in which case $R^1_3$ is any one of the groups given above for $R^1_1$ and $R^1_2$; and
X is oxygen or sulphur and $R^2_4$ is a group —$(CH_2)_tR^1$ wherein t is 1 or 2 and $R^1_6$ is optionally substituted phenyl as defined with respect to formula (I), cyclohexylmethyl or 2-thienylmethyl.

9. 2-Methoxy-5-methylsulphonyl-N-[9-benzyl-9-aza-3-thiabicyclo[3.3.1]non-7β-yl]benzamide, or a pharmaceutically acceptable salt thereof.

10. A compound according to claim 8 having the formula (XI) or a pharmaceutically acceptable salt thereof:

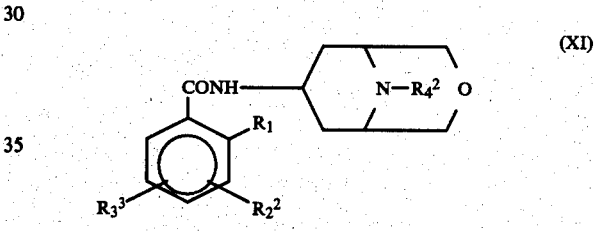

wherein:
X, $R^1_1$ and $R^2_4$ are as defined in claim 8.
$R^2_2$ and $R^3_3$ are the same or different and are $C_{1-6}$ alkoxy or hydrogen; or
$R^1_1$ and $R^2_2$ taken together are methylenedioxy or ethylenedioxy, in which case $R^3_3$ is any one of the groups given above for $R^2_2$ and $R^3_3$.

11. 2,3-Dimethoxy-N-(9-benzyl-9-aza-3-oxabicyclo[3.2.1]non-7β-yl)benzamide, or
2,4,5-Trimethoxy-N-(9-butyl-9-aza-3-oxabicyclo[3.2.1]non-7β-yl)benzamide, or a pharmaceutically acceptable salt thereof.

12. A pharmaceutical composition having dopamine antagonist activity comprising an effective amount of a compound according to claim 1 or a hydrate or a pharmaceutically acceptable salt thereof, together with a pharmaceutically acceptable carrier.

13. A method of treatment of maladies in humans comprising the administration of a composition of claim 12 containing an effective amount of a compound of formula (I) or a pharmaceutically acceptable salt or a hydrate thereof.

* * * * *